(12) United States Patent
Cambron et al.

(10) Patent No.: US 11,986,176 B2
(45) Date of Patent: May 21, 2024

(54) TROCAR SITE CLOSURE CLIP

(71) Applicant: University of Louisville Research Foundation, Inc., Louisville, KY (US)

(72) Inventors: Scott D. Cambron, Louisville, KY (US); Daniel S. Metzinger, Louisville, KY (US); Robert S. Keynton, Goshen, KY (US); Hares A. Patel, Elizabethtown, KY (US); Dakota J. Waldecker, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 275 days.

(21) Appl. No.: 17/059,354

(22) PCT Filed: Jun. 11, 2019

(86) PCT No.: PCT/US2019/036524
§ 371 (c)(1),
(2) Date: Nov. 27, 2020

(87) PCT Pub. No.: WO2019/241229
PCT Pub. Date: Dec. 19, 2019

(65) Prior Publication Data
US 2021/0212673 A1 Jul. 15, 2021

Related U.S. Application Data

(60) Provisional application No. 62/683,298, filed on Jun. 11, 2018.

(51) Int. Cl.
*A61B 17/00* (2006.01)

(52) U.S. Cl.
CPC .......... *A61B 17/0057* (2013.01); *A61B 2017/00004* (2013.01); *A61B 2017/00584* (2013.01);
(Continued)

(58) Field of Classification Search
CPC . A61B 17/0057; A61B 17/064; A61B 17/068; A61B 2017/00004;
(Continued)

(56) References Cited

U.S. PATENT DOCUMENTS 4,586,503 A * 5/1986 Kirsch ................... A61B 17/30
606/151
4,592,356 A * 6/1986 Gutierrez ........... A61B 17/3403
606/221
(Continued)

OTHER PUBLICATIONS

European Search Report, dated Jan. 17, 2022—EP application No. 19 81 9785 Applicant: University of Louisville Research Foundation, Inc.
(Continued)

*Primary Examiner* — Mohamed G Gabr
(74) *Attorney, Agent, or Firm* — Dentons Bingham Greenebaum LLP; Brian W. Chellgren

(57) ABSTRACT

A trocar site closure clip includes a generally triangular central body, a pair of arms extending from the body, and an elongated support extending from the body between the arms. In use, the clip is advanced into a patient through a trocar, the trocar removed, then the clip partially retracted to engage and pierce the patients tissue. The biodegradable clip remains in the patients tissue, at least partially blocking the trocar site, and degrades over time as the patient heals.

13 Claims, 17 Drawing Sheets

(52) U.S. Cl.
CPC ............... *A61B 2017/00637* (2013.01); *A61B 2017/00654* (2013.01); *A61B 2017/00668* (2013.01)

(58) Field of Classification Search
CPC .......... A61B 2017/00526; A61B 2017/00584; A61B 2017/00637; A61B 2017/00654; A61B 2017/00668; A61B 2017/0645
See application file for complete search history.

(56) References Cited

U.S. PATENT DOCUMENTS

| | | | | |
|---|---|---|---|---|
| 5,089,009 | A | * | 2/1992 | Green ................... A61B 17/064 606/220 |
| 5,478,354 | A | | 12/1995 | Tovey |
| 5,941,890 | A | * | 8/1999 | Voegele ................. A61B 90/39 606/220 |
| 9,149,272 | B2 | | 10/2015 | Sherts et al. |
| D804,666 | S | | 12/2017 | Guo et al. |
| 2007/0198058 | A1 | | 8/2007 | Gelbart |
| 2014/0343603 | A1 | | 11/2014 | Metzinger |
| 2016/0022252 | A1 | * | 1/2016 | Zhang .............. A61B 17/06066 606/213 |
| 2017/0209150 | A1 | * | 7/2017 | Shelton, IV ......... A61B 17/122 |

OTHER PUBLICATIONS

International Search Report and Written Opinion, dated Sep. 20, 2019—International application No. PCT/US2019/036524; Applicant: University of Louisville Research Foundation, Inc.

* cited by examiner

TROCAR SITE CLOSURE CLIP

This application claims the benefit of U.S. provisional patent application Ser. No. 62/683,298, filed 11 Jun. 2018, for TROCAR SITE CLOSURE CLIP, incorporated herein by reference.

FIELD OF THE INVENTION

A trocar site closure clip includes a generally triangular central body, a pair of arms extending from the body, and an elongated support extending from the body between the arms. In use, the clip is advanced into a patient through a trocar, the trocar removed, then the clip partially retracted to engage and pierce the patient's tissue. The biodegradable clip remains in the patient's tissue, at least partially blocking the trocar site, and degrades over time as the patient heals.

BACKGROUND

Laparoscopy has gained widespread acceptance as a replacement for open abdominal surgery because of better postoperative outcomes such as less pain, faster recovery, and lower risk of incisional hernias. Laparoscopy utilizes small incisions in the abdomen (or other body part) to insert a trocar, a medical instrument with a sharply pointed end, often three sided, which is used inside a hollow cylinder (cannula) to introduce the trocar into blood vessels or body cavities. In the industry, the cannula and pointed instrument together, the pointed instrument alone, or the cannula alone may be referred to as a trocar. The pointed instrument is often passed inside a central channel of the cannula, forming an opening in the patient, and is then removed. The central channel of the cannula then functions as a portal for the subsequent placement of other devices, such as a chest drain, port, intravenous cannula, etc., into the patient's body. Trocar sites are the openings made in a patient's body by the trocar.

Laparoscopy allows for intricate procedures to be performed, however larger trocars are often required to execute complex surgeries. Use of larger trocars requires larger trocar sites, which results in an increase in the possibility of complications following surgery. These complications can include incisional bowel herniation (hernia) and small bowel obstruction (SBO).

The closure of laparoscopic trocar sites is helpful in reducing such complications. The risk of hernia following laparoscopic surgery (i.e. trocar site hernia or TSH) has been known since 1967. Despite this length of time, data is still sparse and based mostly on retrospective studies with a short and poorly defined follow-up. Surgical approaches and patient-related co-morbidity have also been suggested as risk factors for development of TSH. Controversies also exist regarding both prevention and repair of TSH. Trocar complications occur in approximately 1% to 6% of patients. Herniation associated with laparoscopic trocar sites can occur with incisions as small as 3 mm. Studies have recommended that all 10 and 12 mm trocar sites in adults and all 5 mm trocar sites in children be closed, incorporating the peritoneum into the fascial closure. One study found TSHs to have an incidence of 0.23% at 10 mm port sites and 1.9% at 12 mm port site. This incidence markedly increases to 6.3% for obese patients with a body mass index (BMI) greater than 30.

A number of techniques and devices have been developed to facilitate trocar site closure. Surgical techniques using small retractors and specially curved needles are available. However, using these pose some degree of technical difficulty and can be ineffective with thicker abdominal walls. There are also a number of needle-based devices that puncture the fascia by inserting the needle into the skin incision, piercing the fascia and peritoneum along with suture material, and bringing it out on the other side of the trocar site. However, most of the devices on the market are cumbersome to use, require a learning curve for proficient use, and cause trocar site pain due to the incorporation of the peritoneum into the closure. In addition, there is a lack of standardization as to suturing technique.

SUMMARY

The inventors have discovered that trocar sites do not need to be fully closed on the fascial layer, but simply blocked at the site where the trocar penetrated the abdominal wall. By sufficiently blocking the opening, post-operative herniation can be significantly reduced.

In some embodiments, the present invention comprises a trocar site closure clip including a central body including an apex and a base opposite the apex; a pair of opposing arms extending from the base; and an elongated support positioned between the arms and extending from the base. In further embodiments, the central body is generally triangular in shape, having vertices which may be pointed or rounded. In certain embodiments, each arm tapers from a proximal end attached to the base, to a distal end opposite the proximal end. The some embodiments, the distal end of each arm terminates in a point. In further embodiments, each arm includes an inner surface oriented toward the support and an outer surface opposite the inner surface. In certain embodiments, each arm includes at least one barb, one barb, two barbs, or three barbs on the inner surface of that arm. In some embodiments, the clip is configured to transition between a standard state and a compressed state wherein, in the compressed state, the arms are transiently deformed to approach the support. In further embodiments, the body includes at least one notch extending substantially parallel to the support. In certain embodiments, the clip is formed of a biodegradable material. In some embodiments, the clip is formed of polylactic acid biodegradable biopolymer.

In some embodiments, the present invention comprises a method of at least partially closing a trocar site, the method including providing a trocar site closure clip including: a triangular central body including an apex and a base opposite the apex, a pair of opposing arms extending from the base, and an elongated support positioned between the arms and extending from the base; inserting the clip into a cavity in a tissue by passing the clip through a trocar extending through the tissue; withdrawing the trocar from the tissue, leaving a trocar site in the tissue; partially retracting the clip into the trocar site, the clip thereby engaging the tissue and at least partially blocking the trocar site; and leaving at least a portion of the clip within the trocar site. In further embodiments, the clip is formed of a biodegradable material. In certain embodiments, the clip is formed of a biodegradable polymer. In some embodiments, the clip is formed of polylactic acid biodegradable biopolymer. In further embodiments, partially retracting the clip into the trocar site includes at least partially retracting the support into the trocar site. In certain embodiments, engaging the tissue includes the arms piercing the tissue. In some embodiments, each arm includes at least one barb, one barb, two barbs, or three barbs. In further embodiments, the clip adopts a compressed state while passing through the trocar and returns to a standard state and reverts to a standard state after exiting the trocar. In certain embodiments, when in the compressed state, the arms are transiently deformed to approach the support. In some embodiments, each arm tapers from a proximal end attached to the base, to a distal end opposite the proximal end.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

The end effector shown in FIGS. 5C-5J is depicted as a transparent outline so that the trocar site closure clip remains visible even when held by the end effector.

DETAILED DESCRIPTION OF THE PREFERRED EMBODIMENTS

Figure 1A:
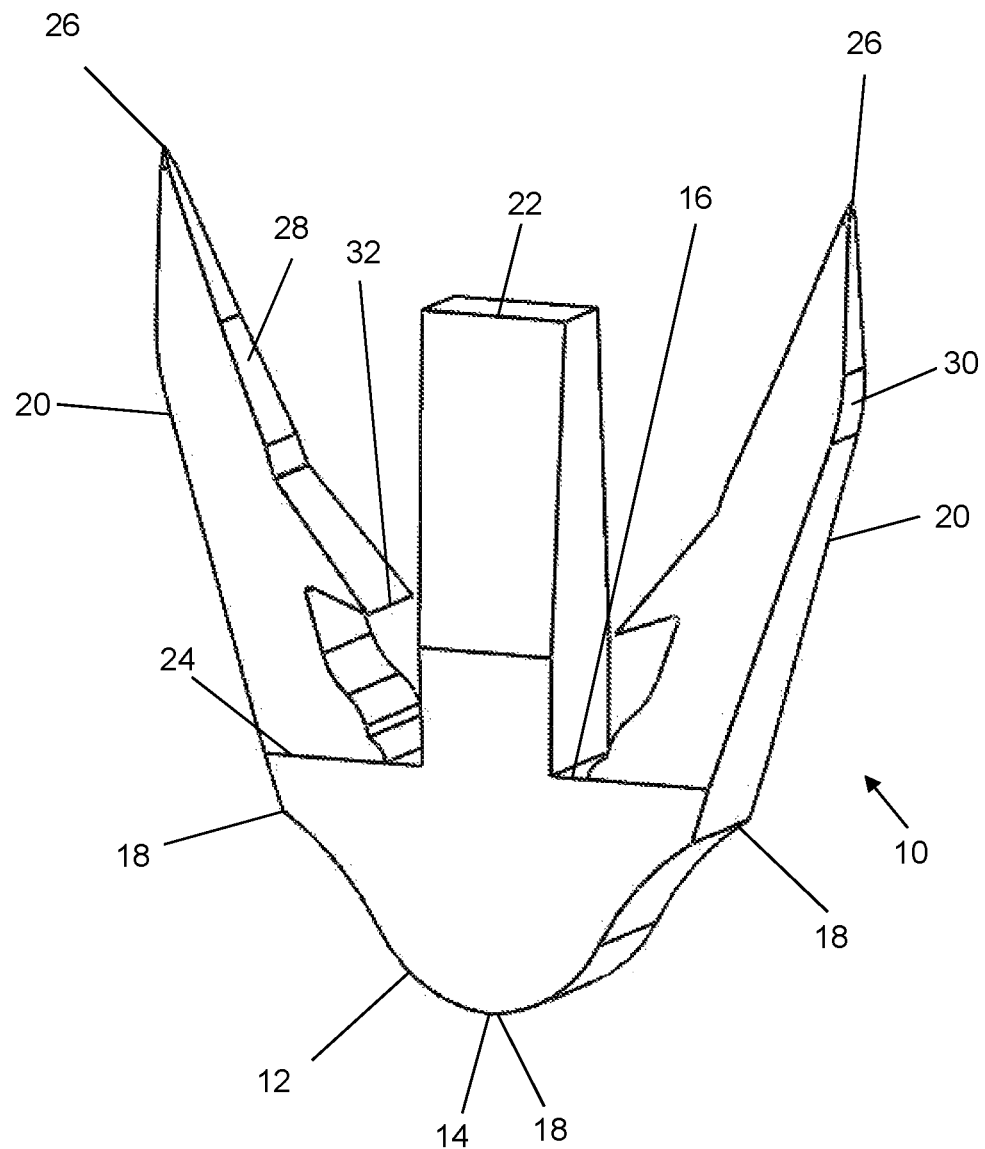
FIG. 1A is a front perspective view of a first embodiment of a trocar site closure clip in a standard state.

A first embodiment of a suture-less trocar site closure clip 10 is shown in FIG. 1A. The clip 10 includes a generally triangular central body 12 including an apex 14 and a base 16 opposite the apex 14. The vertices 18 of the generally triangular central body 12 are pointed in some embodiments and rounded in other embodiments. A pair of opposing arms 20 extend upwards and outwards from the base 16 of the central body 12, such that the body 12 and arms 20 form a V-shape. The clip 10 further includes an elongated support 22 positioned between the arms 20 and extending upwards from the base 16 of the central body 12, such that the support 22 bisects an angle formed by an arm 20, the apex 14, and the other arm 20. In the depicted embodiment, the support 22 tapers as it extends away from the body 12. Each arm 20 tapers from the proximal end 24 of the arm 20 attached to the base 16 of the central body 12, to the distal end 26 of the arm 20 furthest from the central body 12 and opposite the proximal end 24, such that the distal end 26 of each arm 20 terminates in a point. Each arm 20 includes an inner side 28 oriented toward the support 22 and an outer side 30 opposite the inner side 28. In some embodiments, each arm 20 includes at least one barb 32 on the inner side 28. In other embodiments, barbs are omitted. The trocar site closure clip 10 is preferably constructed of a resilient, flexible material, such that the clip 10 may adopt a compressed state, shown in FIG. 1B, wherein the arms 20 are transiently deformed by a compressing force to press closer to the support 22, then return to the standard state shown in FIG. 1A when the compressing force is removed.

Figure 2A:
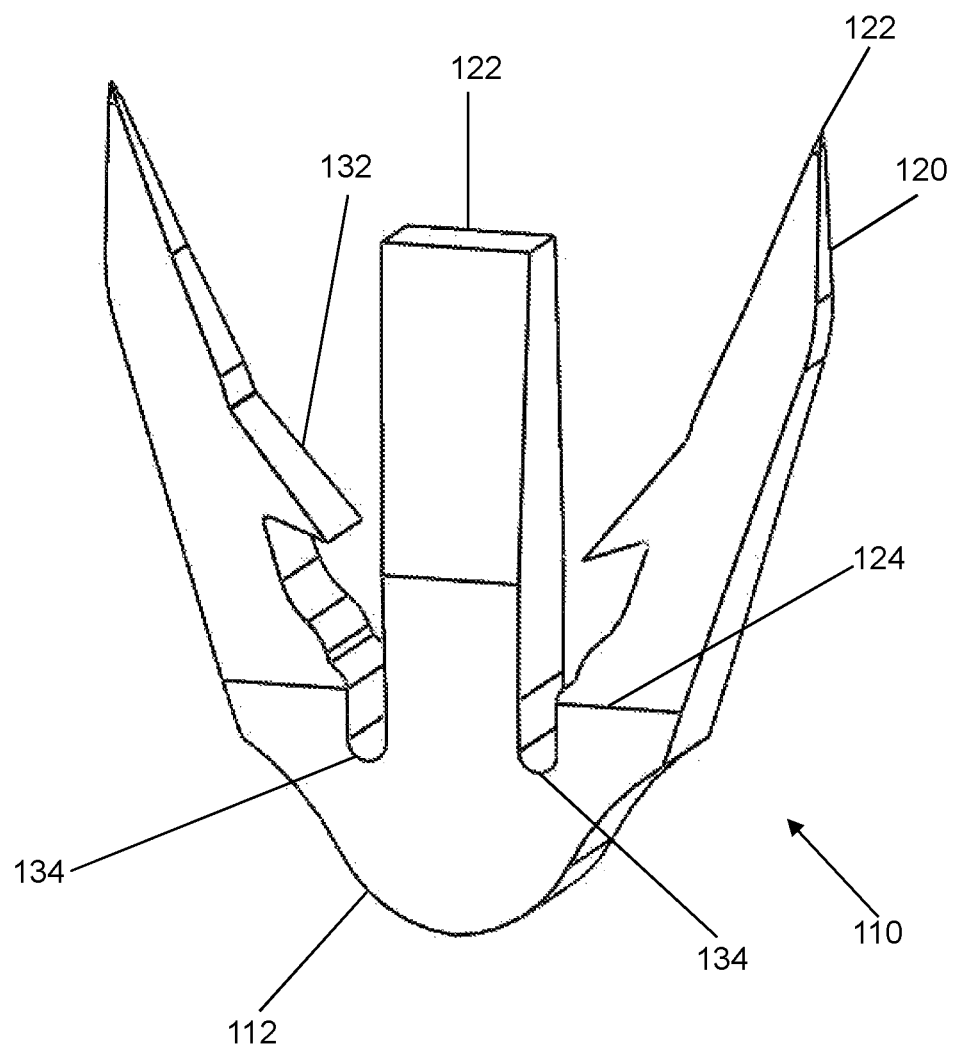
FIG. 2A is a front perspective view of a second embodiment of a trocar site closure clip.
Figure 2B:
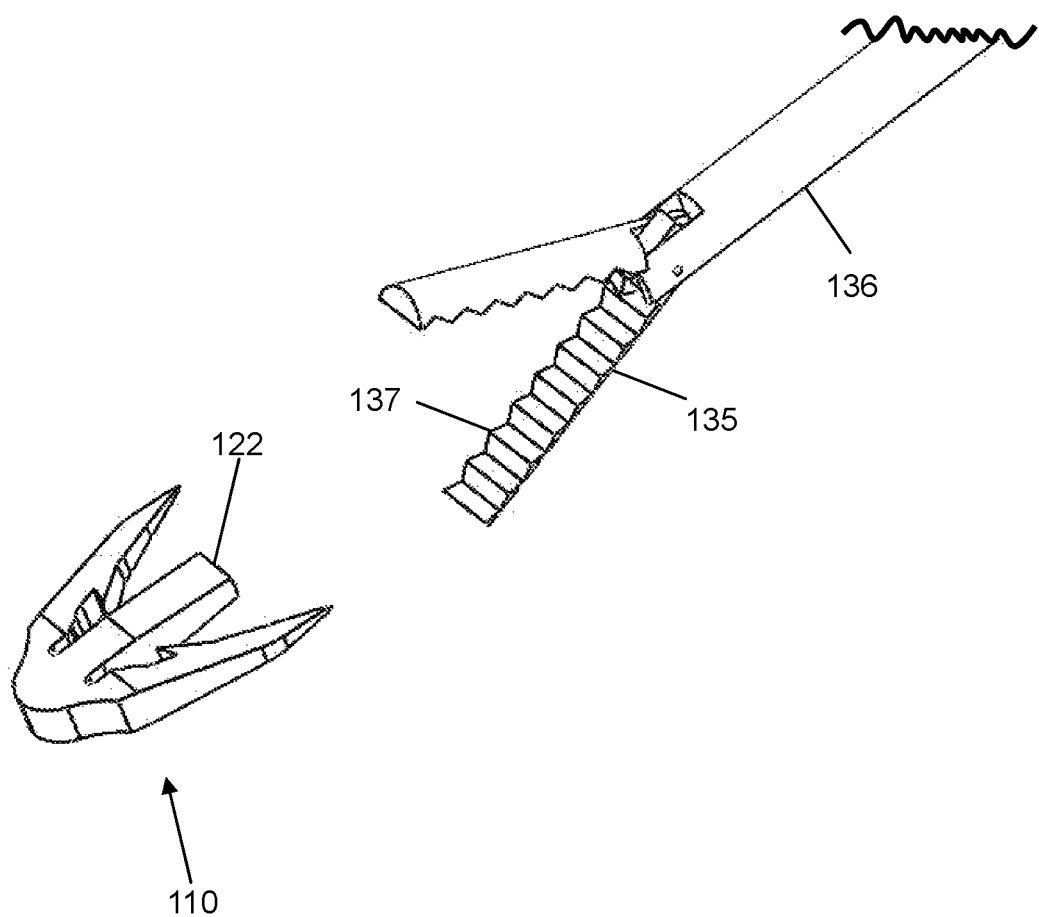
FIG. 2B is a side perspective view of the trocar site closure clip of FIG. 2A and endoscopic forceps.

Referring now to FIG. 2A, a second embodiment of a trocar site closure clip 110 is similar to the first embodiment clip 10. The clip 110 includes stress notches 134 in the central body 112, extending substantially parallel to the elongated support 122, to decrease the strain on the clip 110 when adopting the compressed state. The end effector 135 of endoscopic forceps 136 may be used to grip the support 122 of the clip 110, as shown in FIG. 2B, to transport and position the clip 110. A similar technique and device may be used with the first embodiment clip 10.

Figure 3:
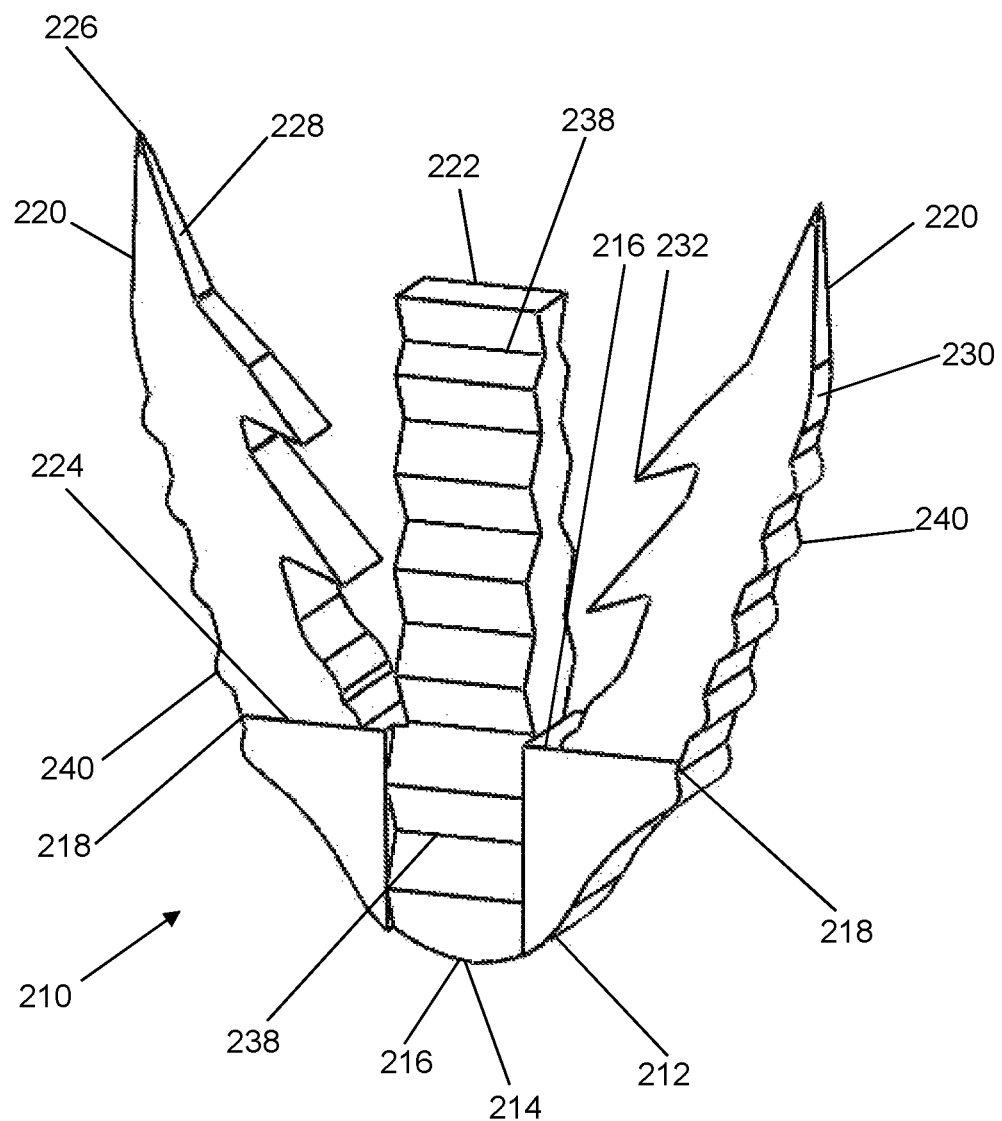
FIG. 3 is a front perspective view of a third embodiment of a trocar site closure clip in a standard state.

A third embodiment of a suture-less trocar site closure clip 210 is shown in FIG. 3. The clip 210 includes a generally triangular central body 212 including an apex 214 and a base 216 opposite the apex 214. The vertices 218 of the generally triangular central body 212 are pointed in some embodiments and rounded in other embodiments. A pair of opposing arms 220 extend upwards and outwards from the base 216 of the central body 212, such that the body 212 and arms 220 form a V-shape. The clip 210 further includes an elongated support 222 positioned between the arms 220 and extending upwards from the base 216 of the central body 212, such that the support 222 bisects an angle formed by an arm 220, the apex 214, and the other arm 220. In this embodiment, the support 222 and a portion of the body 212 include grooves 238 corresponding to serration or "teeth" 137 on the end effector 135 of endoscopic forceps 136 (as shown in FIG. 2B), to improve the grip of end effector 135 on the clip 210. Each arm 220 tapers from the proximal end 224 of the arm 220 attached to the base 216 of the central body 212, to the distal end 226 of the arm 220 furthest from the central body 212 and opposite the proximal end 224, such that the distal end 226 of each arm 220 terminates in a point. Each arm 220 includes an inner side 228 oriented toward the support 222 and an outer side 230 opposite the inner side 228. In some embodiments, each arm 220 includes at least one barb 232 on the inner side 228. In this second embodiment, each arm 220 includes two barbs 232. The clip 210 optionally includes a series of knurls 240 on the outer side 230 of each arm 220 to increase the retention strength of the clip 210.

Figure 4:
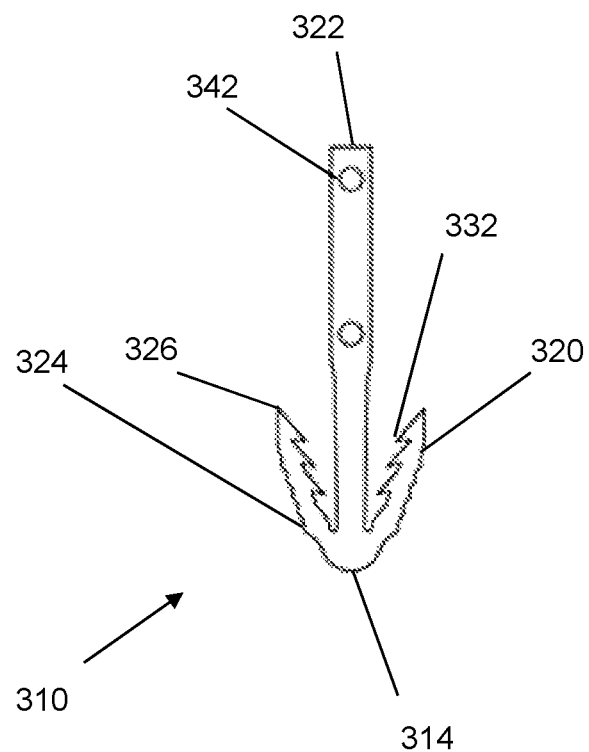
FIG. 4 is a front view of a fourth embodiment of a trocar site closure clip.

A fourth embodiment of a suture-less trocar site closure clip 310 is shown in FIG. 4. This fourth embodiment clip 310 is similar to the second embodiment clip 110, but includes additional barbs 332 on the arms 320 (three barbs instead of one barb) and includes an elongated support 322. In this embodiment, the elongated support 322 is longer than arms 320 and sized such that, when used as described below, the support 322 extends through a trocar site and a portion of the support remains external to the patient. The depicted holes 342 in the elongated support 322 are optional.

Figure 1B:
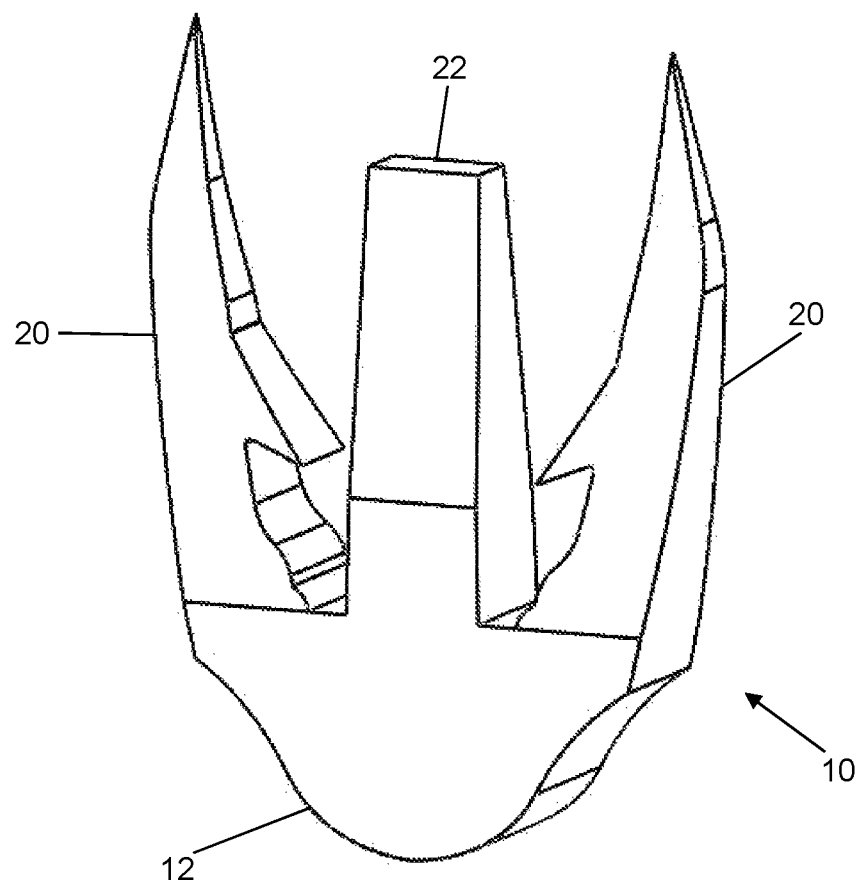
FIG. 1B is a front perspective view of the trocar site closure clip of FIG. 1A in a compressed state.

The trocar site closure clip 10, 110, 210, 310 is preferably constructed of a resilient material, such that the clip 10, 110, 210, 310 may adopt a compressed state, as shown in FIG. 1B, wherein the arms 20, 120, 220, 320 are transiently deformed by a compressing force to press closer to the support 22, 122, 222, 322 then return to the standard state shown in FIGS. 1A, 2A, 3 and 4 when the compressing force is removed.

In some embodiments, the trocar site closure clip 10, 110, 210, 310 is an integral piece. In further embodiments, the clip 10, 110, 210, 310 is formed using additive manufacturing techniques, such as fused filament (3D) printing of the material. In one embodiment, the clip 10, 110, 210, 310 is formed from a PLA (polylactic acid) biodegradable biopolymer using 100% virgin PLA biopolymer resin and optional colorants. In other embodiments, other biodegradable polymers may be used. In one embodiment, a fused deposition modeling printer was used to extrude an ⅛" thick plate of PLA. The PLA was printed using 95% infill. The porosity of the material (infill) may vary to decrease the rate of biodegradation of the clip 10, 110, 210, 310 with a higher porosity (i.e., lower infill) resulting in faster degradation. In some embodiments, the clip 10, 110, 210, 310 has an infill percentage from 50% to 100%. In further embodiments, the clip 10, 110, 210, 310 has an infill percentage between 70% and 100%. In certain embodiments, the clip 10, 110, 210, 310 has an infill percentage between 90% and 100%. In some embodiments, the clip 10, 110, 210, 310 has an infill percentage of about 95% in a 45° rectilinear pattern.

The clip 10, 110, 210, 310 was then laser cut from the PLA sheet printed in the fused filament printer. The distal ends 26, 126, 226, 326 of the arms 20, 120, 220, 320 were then cut at an angle to sharpen the distal ends 26, 126, 226, 326 into points. In further embodiments (not shown), the outer sides, inner sides, or both may be sharpened as well. The arms 20, 120, 220, 320 were then sanded, abraded or cut to create a taper from the proximal 24, 124, 224, 324 end to the distal end 26, 126, 226, 326 of each arm 20, 120, 220, 320 while maintaining the sharpened distal end 26, 126, 226, 326. Next, the arms 20, 120, 220, 320 were sanded with 220 grade sand paper, followed by 1600 grade sand paper, to remove surface inconsistencies. In some embodiments, the apex 14, 114, 214, 314 may also be sanded to a point. For the third embodiment, after the arms 220 were sanded down to a smooth finish, the support 222 and body 212 of the clip 210 were heated using a heat gun to make them pliable. The end effector 135 (or jaws) of endoscopic forceps 136 were then closed on the heated support 222 and body 212 thereby forming grooves 238 in the support 222 and body 212 corresponding to the teeth 137 of the end effector 135. Optionally, clips 10, 110, 210, 310 may be treated with acetone to soften the PLA and increase the flexibility of the arms 20, 120, 220, 320, easing the transitions between the standard and compressed state. In other embodiments, the clip 10, 110, 210, 310 may be manufactured by injection molding or other techniques known in the art.

Figure 5A:
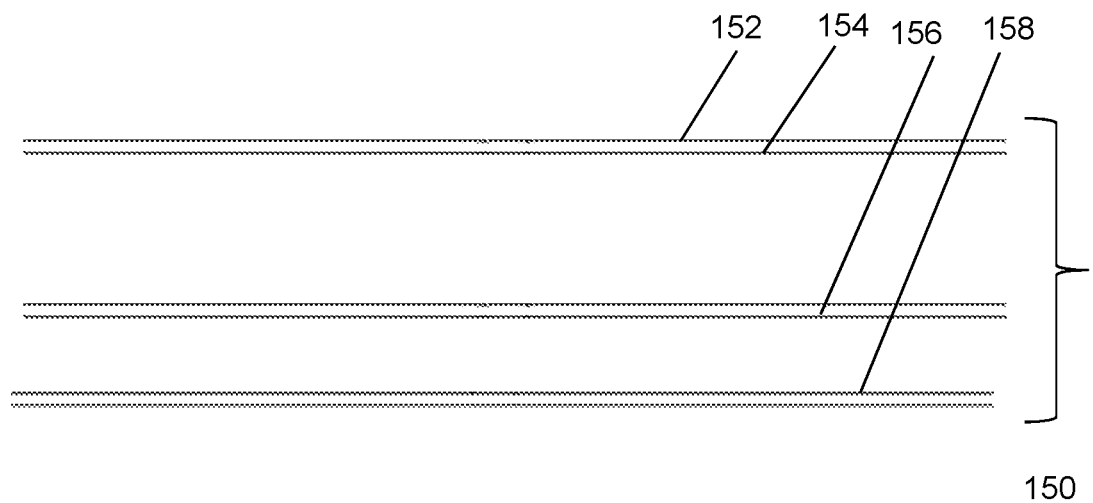
FIG. 5A is a schematic depiction of a patient's abdominal wall.
Figure 5B:
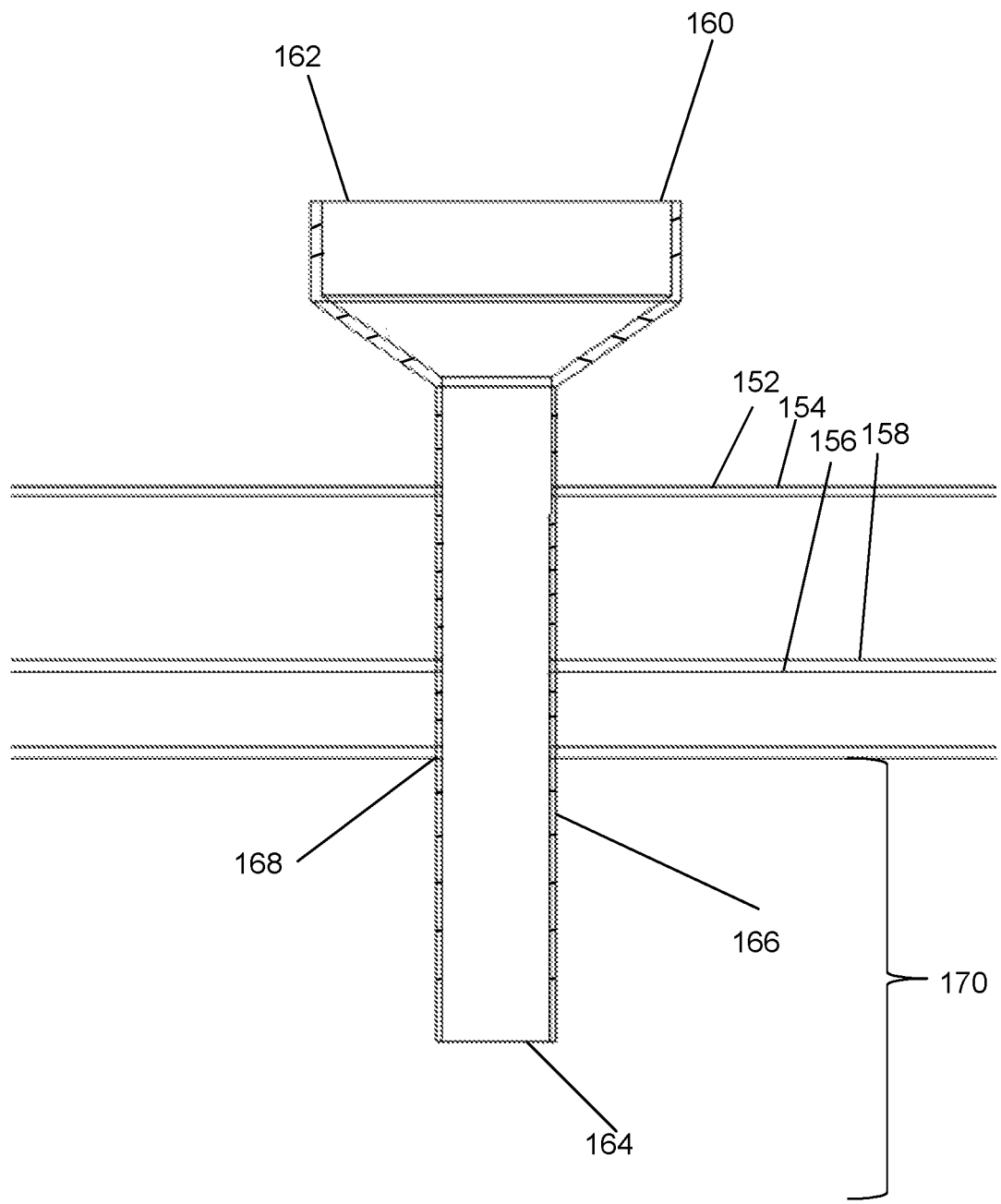
FIG. 5B is a schematic depiction of the trocar with the distal end of the trocar inserted through the patient's abdominal wall.

Referring now to FIGS. 5A and 5B, a patient's abdominal wall 150 includes a skin layer 152, an adipose tissue layer 154, a muscular layer 156, and a peritoneal layer 158 (these layers are specified for example purposes only, additional layers are also present). A trocar 160 includes a proximal end 162, a distal end 164, and a passageway 166 extending between the proximal end 162 and the distal end 164. An opening in a patient formed by a trocar is referred to as a trocar site 168.

Figure 5C:
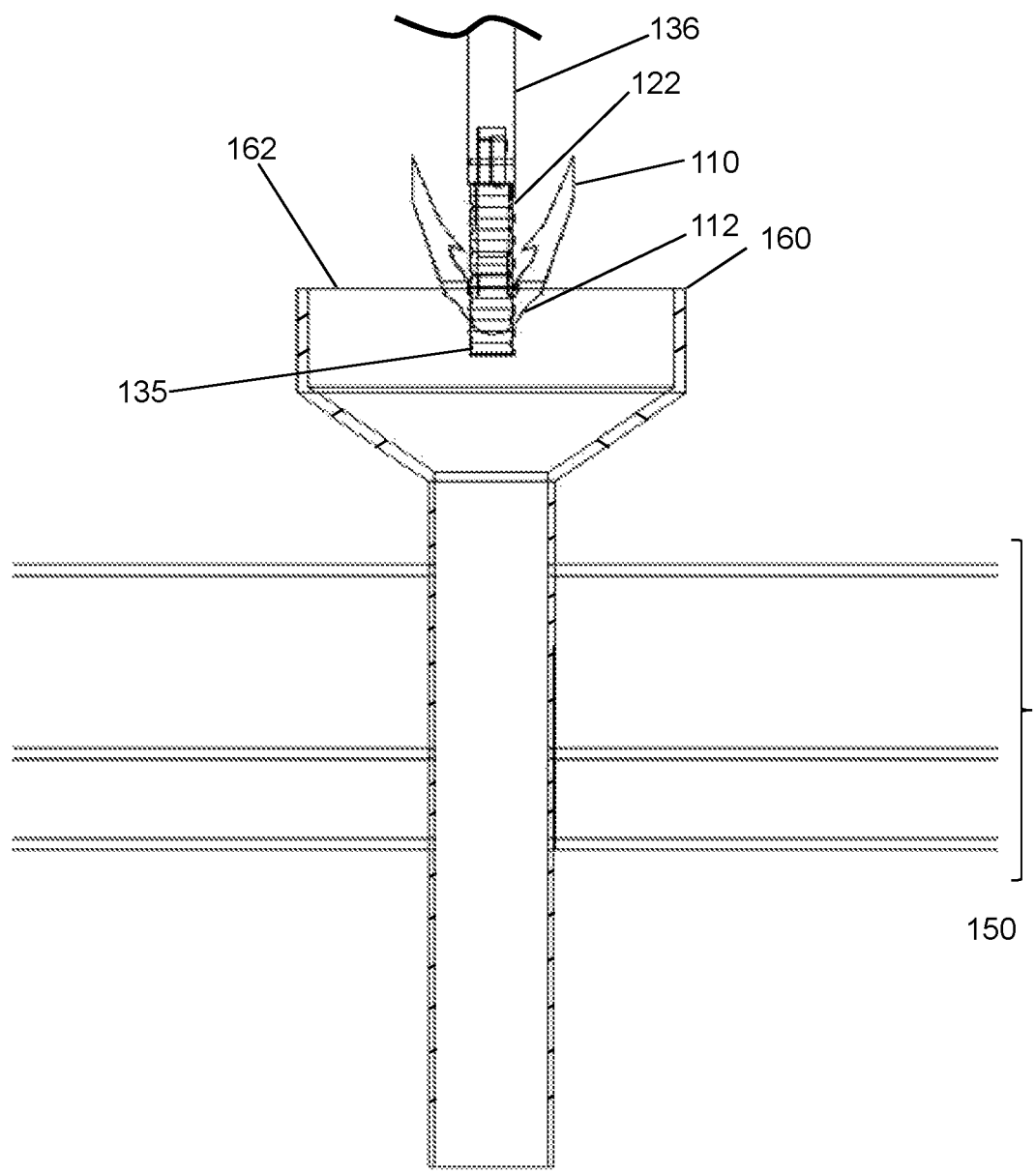
FIG. 5C is a schematic depiction of a trocar site closure clip held in endoscopic forceps advancing toward the proximal end of the trocar.
Figure 5D:
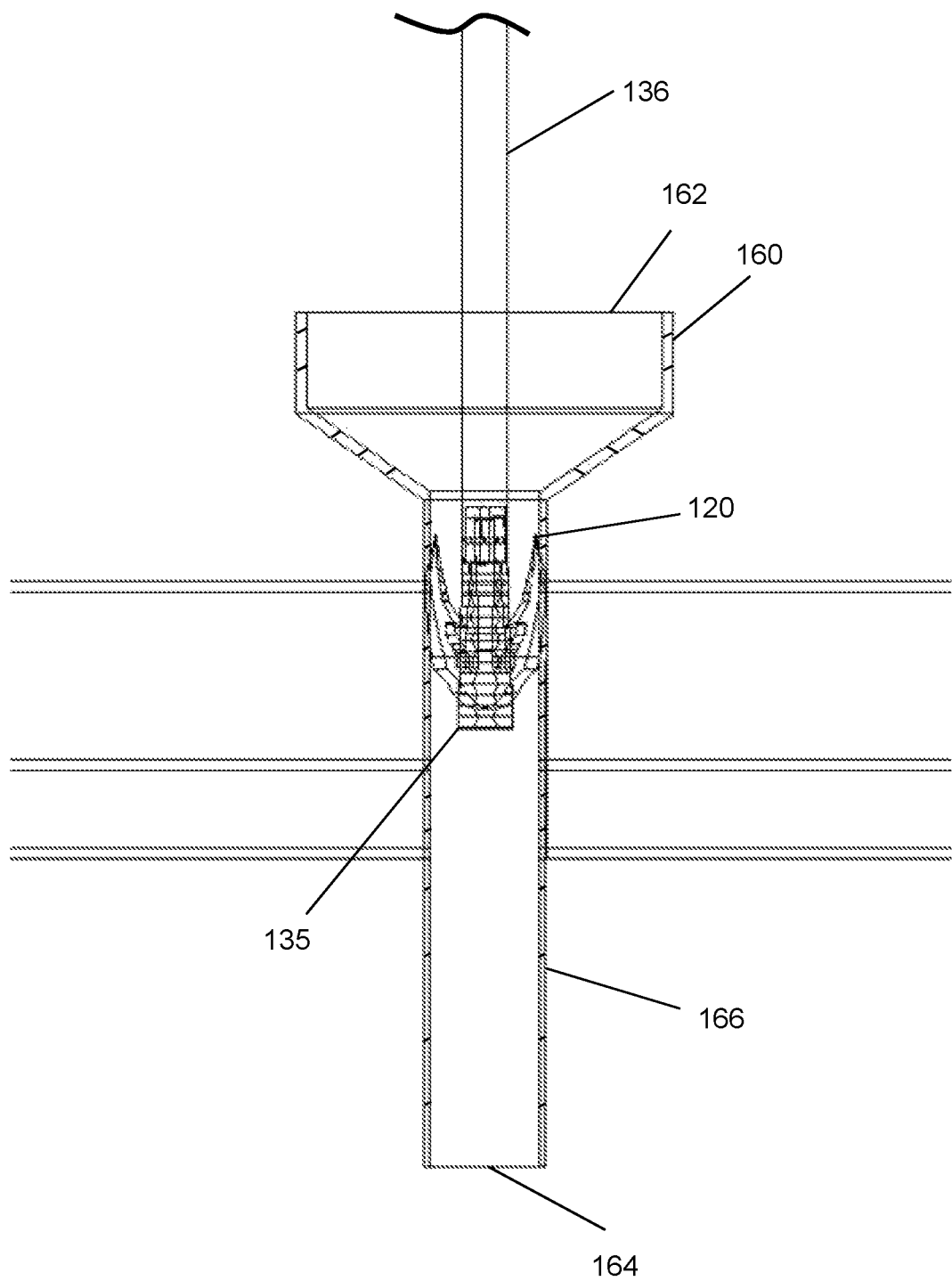
FIG. 5D is a schematic depiction of the clip inserted into the trocar, the clip being in the compressed state.
Figure 5E:
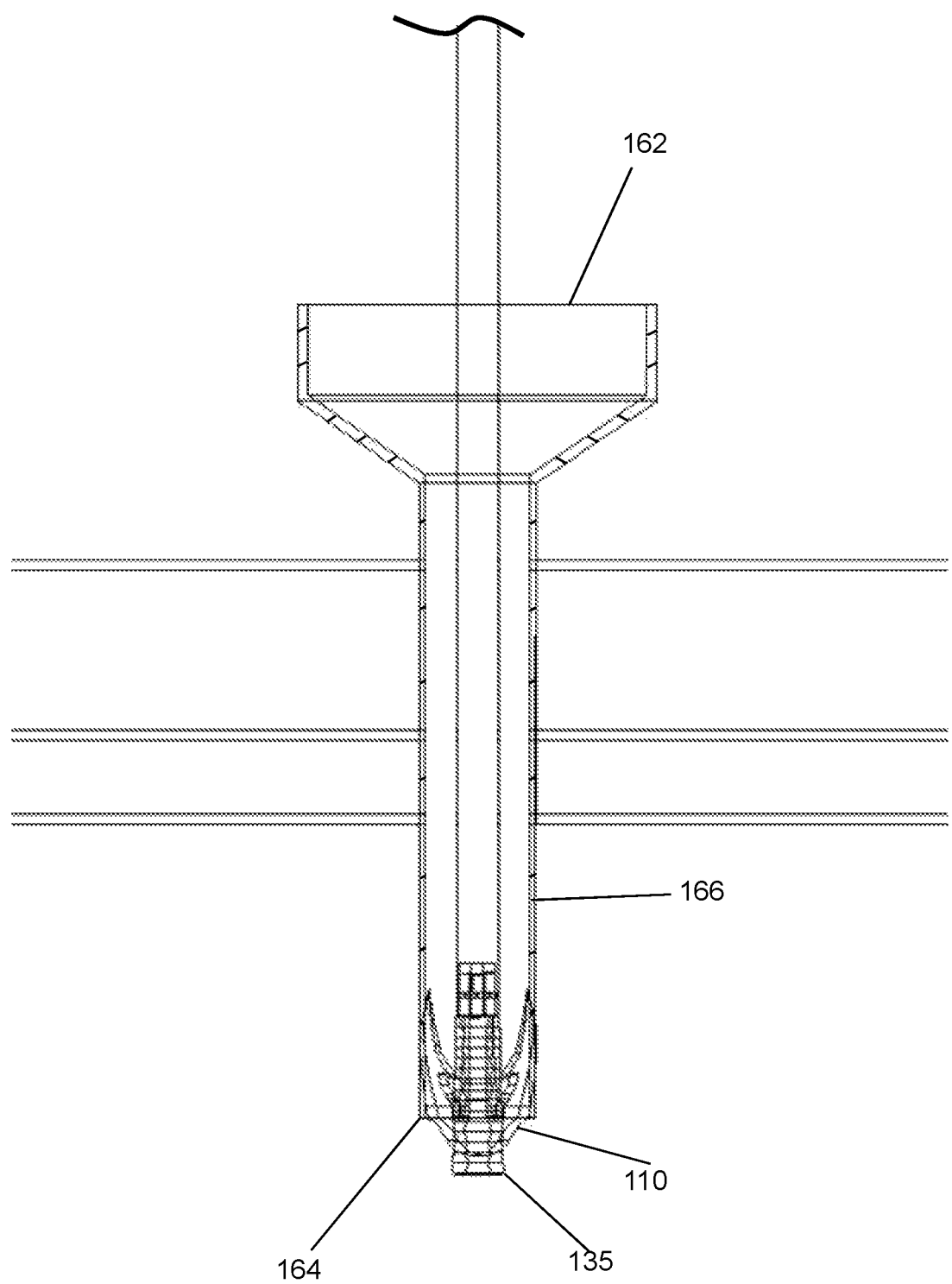
FIG. 5E is a schematic depiction of the clip emerging from the distal end of the trocar.
Figure 5F:
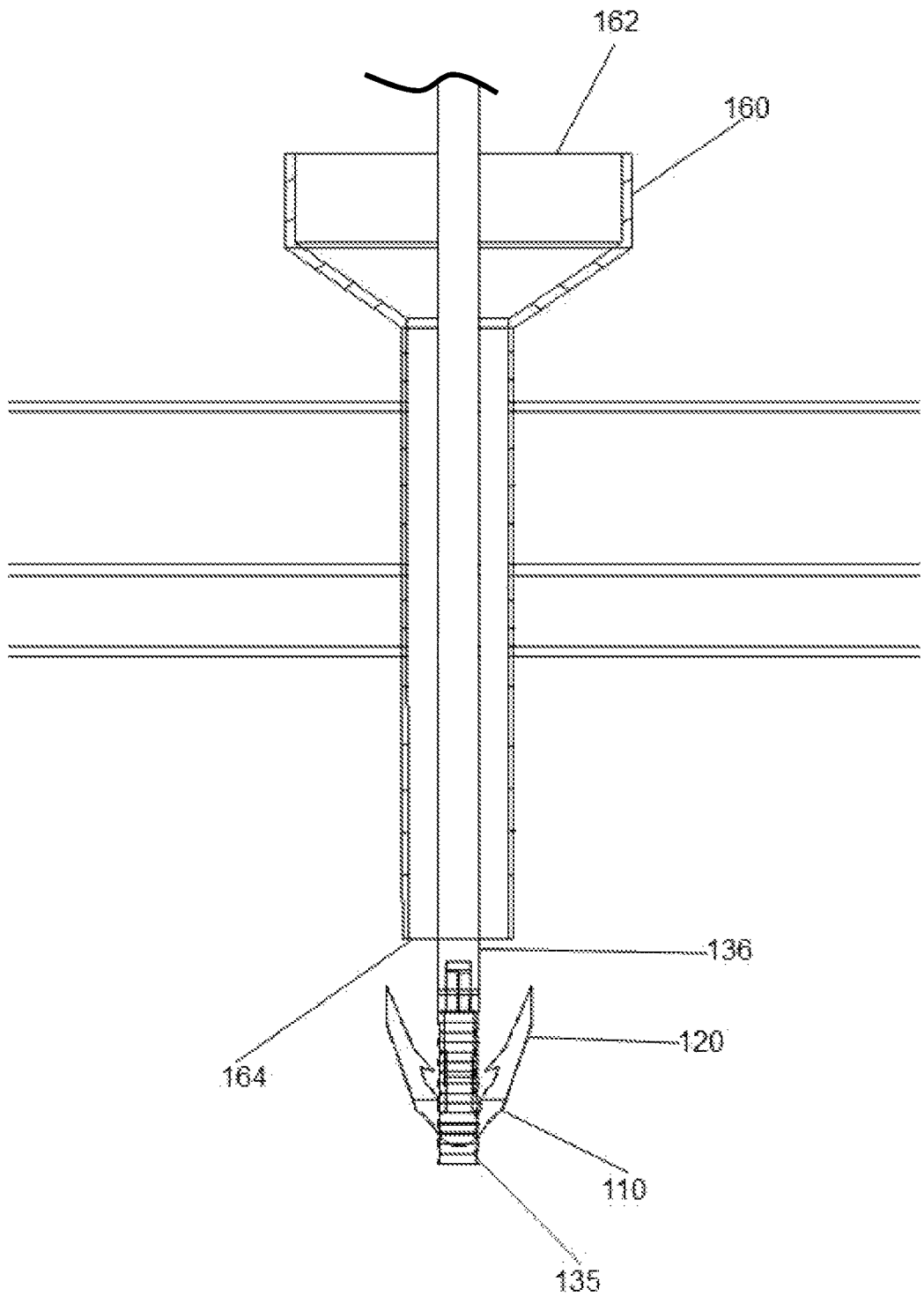
FIG. 5F is a schematic depiction of the clip emerged from the distal end of the trocar, the clip having returned to the standard state.
Figure 5G:
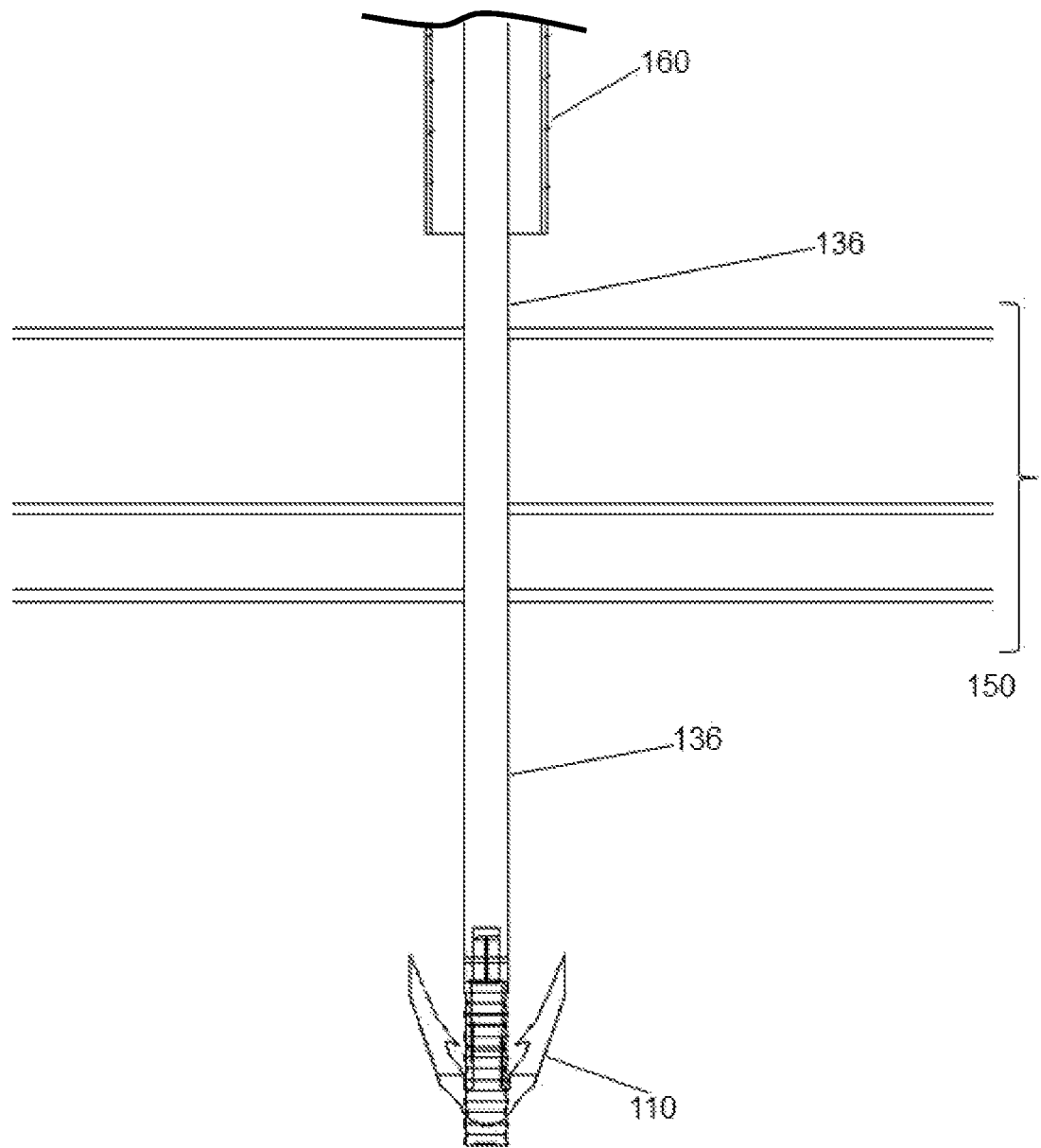
FIG. 5G is a schematic depiction of the removal of the trocar from the patient's abdominal wall.

An exemplary method of using the trocar site 168 closure clip 110 is depicted sequentially in FIGS. 5A-5K. As shown in FIGS. 5A and 4B, a trocar 160 is inserted into a tissue, such as a patient's abdominal wall 150, sequentially piercing the patient's skin layer 152, adipose tissue layer 154, muscular layer 156 and peritoneal layer 158, to enter the abdominal cavity 170. As shown in FIGS. 5C and 5D, the support 122 and body 112 of a trocar site closure clip 110 are gripped by the end effector 135 of endoscopic forceps 136, which are advanced towards and are inserted into the proximal end 162 of the trocar 160. The diameter of the passageway 166 is less than the width of the arms 120 in the standard state. As such, the clip 110 adopts a compressed state as the clip 110 is advanced through the passageway 166, as shown in FIGS. 5D and 5E. As shown in FIG. 5F, the clip 110 emerges from the distal end 164 of the trocar 160 and resiliently returns from the compressed state to the standard state. As shown in FIG. 5G, the trocar 160 is then withdrawn from the patient's abdominal wall 150, leaving the endoscopic forceps 136 extending through the abdominal wall 150.

Figure 5H:
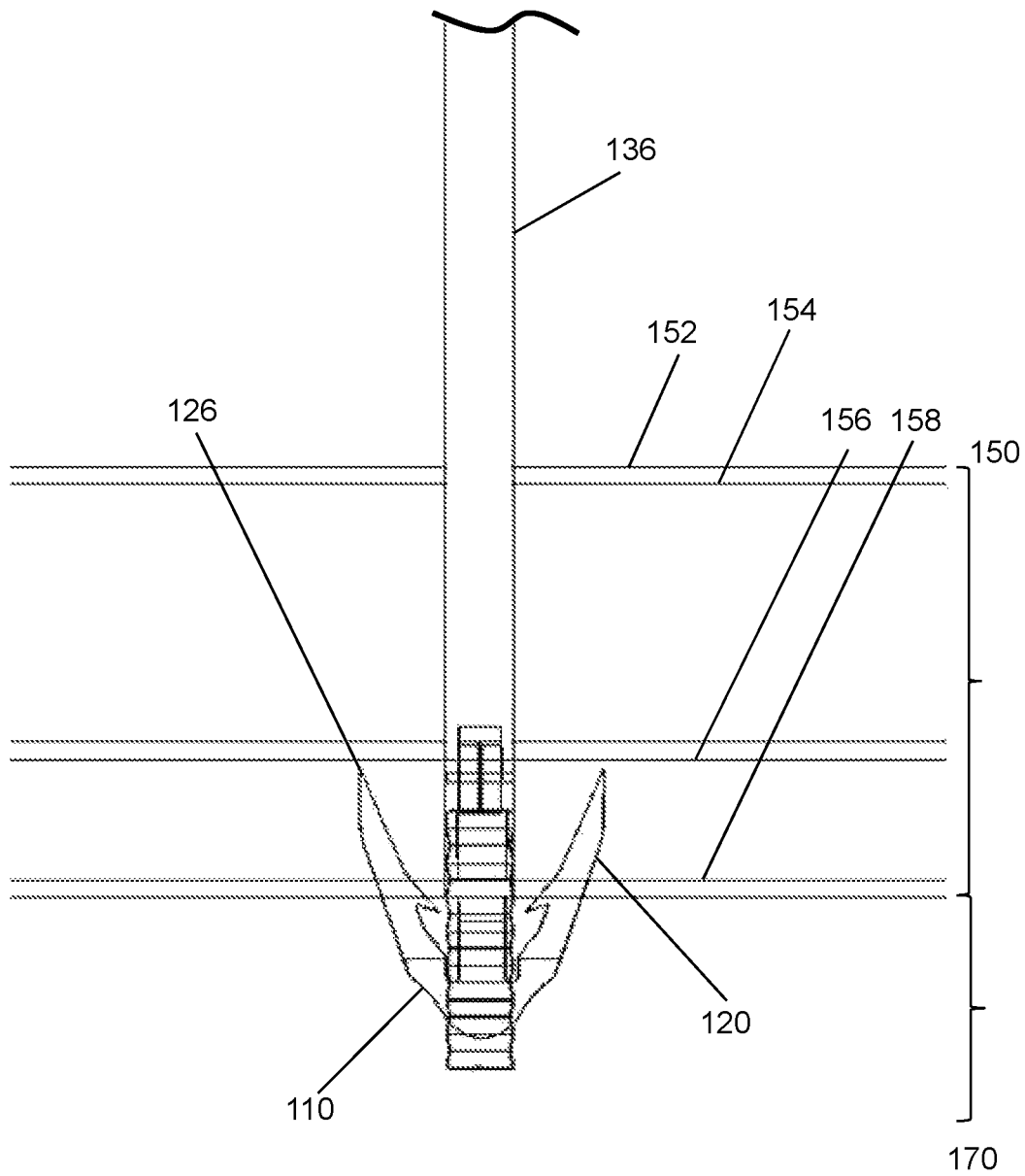
FIG. 5H is a schematic depiction of the retraction of the endoscopic forceps, the arms of the clip engaging and piercing the patient's peritoneal layer.
Figure 5I:
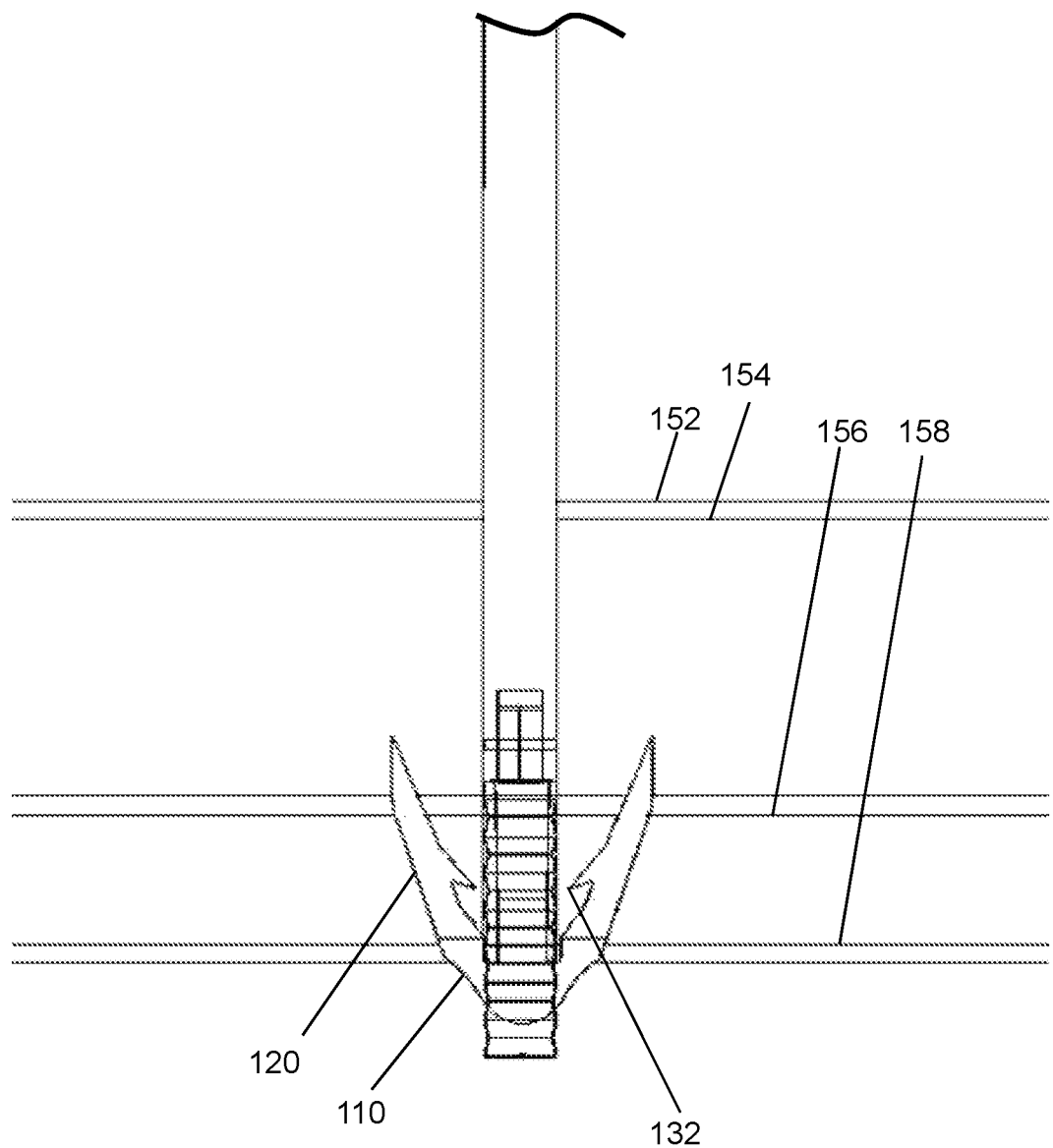
FIG. 5I is a schematic depiction of further retraction of the endoscopic forceps, the arms of the clip engaging the piercing the patient's muscular tissue.
Figure 5J:
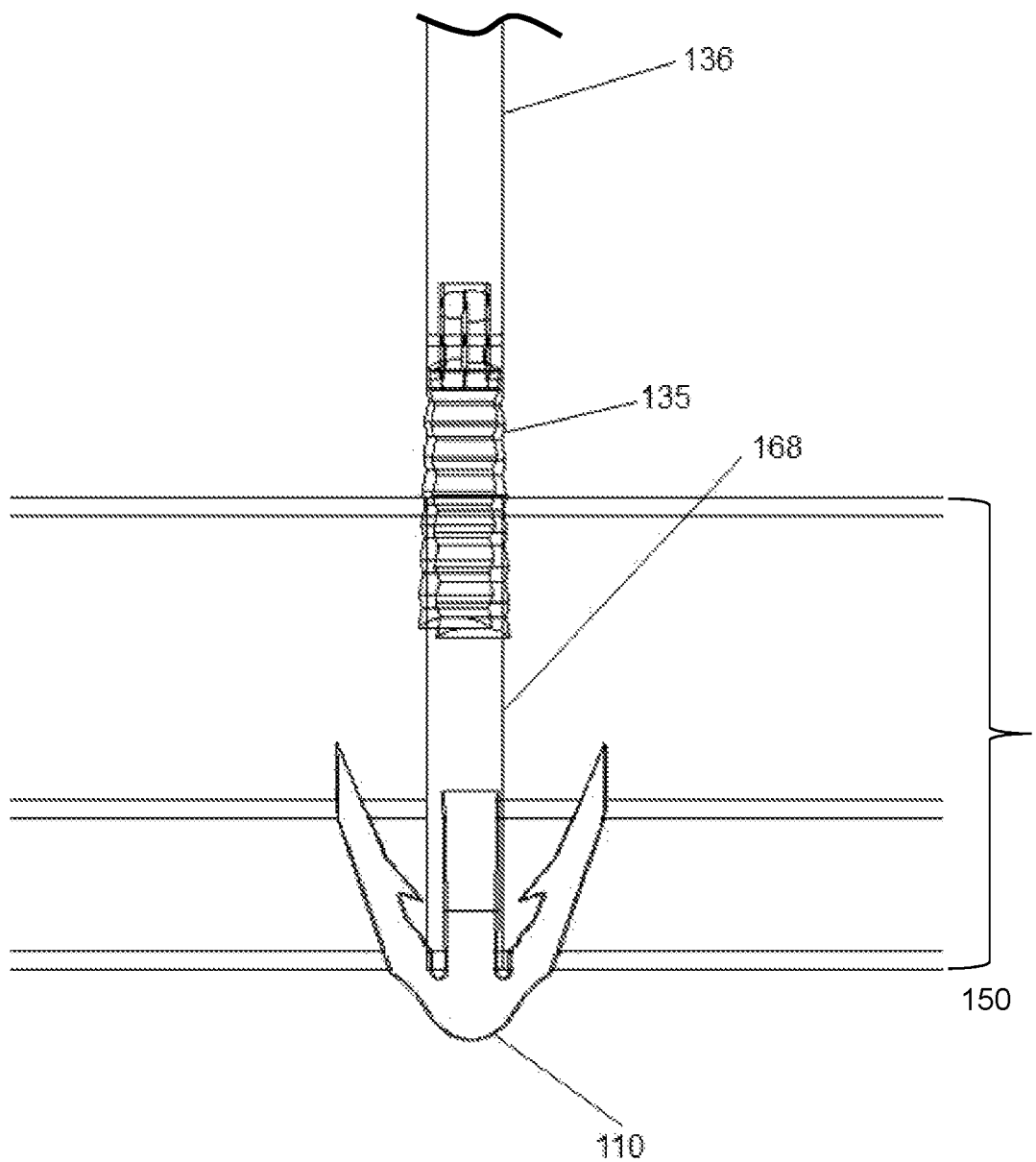
FIG. 5J is a schematic depiction of the release of the clip by the endoscopic forceps and further retraction of the endoscopic forceps, the clip being retained in the patient's abdominal wall.
Figure 5K:
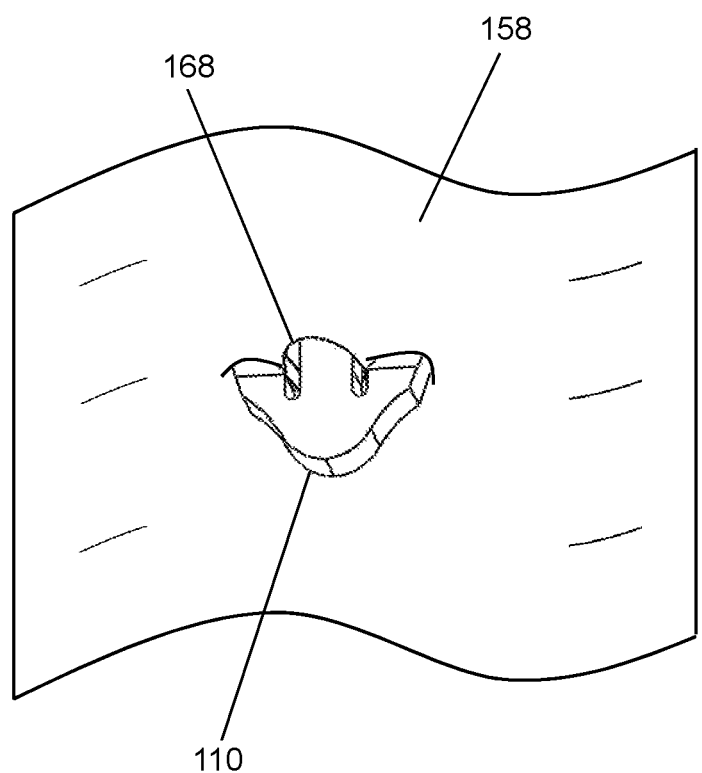
FIG. 5K is a schematic depiction of the clip embedded in the patient's abdominal wall.

As shown in FIG. 5H, retraction of the endoscopic forceps 136 causes the arms 120 of the clip 110 to engage the peritoneal layer 158 and muscular layer 156 of the patient's abdominal wall 150. The sharpened distal ends 126, and optionally sharpened sides of the arms 120, allow the arms 120 to pierce the abdominal wall 150, reducing the effects of tissue compliance, minimizing the generation of a moment force on the clip 110 to prevent rotation, and facilitating the engagement of the clip 110. The angular barbs 132 further engage the patient's abdominal wall 150, retaining the clip 110 at least partially within the abdominal wall 150 and preventing the clip 110 from returning into the abdominal cavity 170. Further retraction of the endoscopic forceps 136, as shown in FIG. 5I, causes the arms 120 to engage and pierce the patient's adipose layer 154 and the barbs 132 to engage the muscular layer 156. The trocar site 168 closure clip 110 can be released from the endoscopic forceps 136 by torqueing, manually releasing, or snapping of the end effector 135 off of the endoscopic forceps 136. As shown in FIG. 5J, in this exemplary method, the end effector 135 of the endoscopic forceps 136 releases the clip 110 and the endoscopic forceps 136 are withdrawn from the abdominal wall 150, leaving the clip 110 at least partially within and occluding the trocar site 168.

While the method shown in FIGS. 5A-5J depicts use of the second embodiment of the clip 110, the disclosed method may also be used with other embodiments of the clip 10, 210, 310. As previously discussed, the fourth embodiment of the clip 310 is designed with an elongated support 322, such that the support 322 would extend through the trocar site external to the patient. The medical professional using the clip 310 could grip the portion of the support 322 external to the patient, break the support 322, and leave the body 312, arms 320, and a portion of the support 322 within the patient to occlude the trocar site.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method of at least partially closing a trocar site, comprising:
   providing a trocar site closure clip including:
      a triangular central body including an apex and a base opposite the apex,
      a pair of opposing arms extending from the base,
      an elongated support positioned between the arms and extending from the base,
      wherein each arm includes an inner side oriented toward the support and an outer side opposite the inner side, and
      wherein each arm includes a series of knurls on the outer side of that arm;
   inserting the clip into a cavity in a tissue by passing the clip through a trocar extending through the tissue;
   withdrawing the trocar from the tissue, leaving a trocar site in the tissue;
   partially retracting the clip into the trocar site, the clip thereby engaging the tissue and at least partially blocking the trocar site; and
   leaving at least a portion of the clip within the trocar site.

2. The method of claim 1, wherein the clip is formed of a biodegradable material.

3. The method of claim 1, wherein the clip is formed of a biodegradable polymer.

4. The method of claim 1, wherein the clip is formed of polylactic acid biodegradable biopolymer.

5. The method of claim 1, wherein partially retracting the clip into the trocar site includes at least partially retracting the support into the trocar site.

6. The method of claim 1, wherein engaging the tissue includes the arms piercing the tissue.

7. The method of claim 1, wherein each arm includes at least one barb on the inner side of that arm.

8. The method of claim 1, wherein the clip adopts a compressed state while passing through the trocar and returns to a standard state after exiting the trocar.

9. The method of claim 8, wherein, in the compressed state, the arms are transiently deformed to approach the support.

10. The method of claim 1, wherein each arm tapers from a proximal end attached to the base, to a distal end opposite the proximal end.

11. A method of at least partially closing a trocar site, comprising:
    providing a trocar site closure clip including:
       a triangular central body including an apex and a base opposite the apex,
       a pair of opposing arms extending from the base,
       an elongated support positioned between the arms and extending from the base;
    gripping the support of the clip using an end effector;
    inserting the clip into a cavity in a tissue by passing the clip and end effector through a trocar extending through the tissue;
    withdrawing the trocar from the tissue, leaving a trocar site in the tissue;
    partially retracting the clip into the trocar site, the clip thereby engaging the tissue and at least partially blocking the trocar site;
    releasing the support from the end effector; and
    leaving at least a portion of the clip within the trocar site.

12. The method of claim 11, wherein the support and at least a portion of the body of the clip include grooves corresponding to serration on the end effector.

13. The method of claim 11, wherein the end effector is the end effector of endoscopic forceps.

* * * * *